United States Patent [19]

Convents et al.

[11] Patent Number: 5,668,073
[45] Date of Patent: Sep. 16, 1997

[54] DETERGENT COMPOUNDS WITH HIGH ACTIVITY CELLULASE AND QUATERNARY AMMONIUM COMPOUNDS

[75] Inventors: Andre Christian Convents, Diegem; Alfred Busch, Londerzeel; Andre Cesar Baeck, Bonheiden, all of Belgium

[73] Assignee: The Procter & Gamble Company, Cincinnati, Ohio

[21] Appl. No.: 666,147

[22] Filed: Jun. 19, 1996

Related U.S. Application Data

[63] Continuation of Ser. No. 290,712, filed as PCT/US92/01179 Feb. 15, 1992 published as WO93/16158 Aug. 19, 1993.

[30] Foreign Application Priority Data

Nov. 6, 1991 [EP] European Pat. Off. ............ 91202881

[51] Int. Cl.$^6$ ............... C11D 3/386; C11D 1/88
[52] U.S. Cl. ............... 502/320; 502/330
[58] Field of Search ............... 510/276, 320, 510/330

[56] References Cited

U.S. PATENT DOCUMENTS

| | | | |
|---|---|---|---|
| 4,272,306 | 6/1981 | Reisinger, Jr. ............ | 148/16.5 |
| 4,435,307 | 3/1984 | Barbesgaard et al. ............ | 252/174.12 |
| 4,664,817 | 5/1987 | Wixon ............ | 252/8.8 |
| 4,806,260 | 2/1989 | Broze et al. ............ | 252/8.8 |

FOREIGN PATENT DOCUMENTS

| | | | |
|---|---|---|---|
| 177165 | 4/1986 | European Pat. Off. ........ | C11D 3/386 |
| 0177165 | 9/1986 | European Pat. Off. . | |
| 220016 | 4/1987 | European Pat. Off. ........ | C11D 3/386 |
| 0269168 | 11/1987 | European Pat. Off. . | |
| 269168 | 6/1988 | European Pat. Off. ........ | C11D 3/386 |
| 117785 | 5/1985 | Japan . | |
| 61/276897 | 12/1986 | Japan ............... | C11D 3/38 |
| 62/265400 | 10/1987 | Japan ............... | C11D 10/02 |
| 9117243 | 11/1991 | WIPO . | |
| WO 91/17243 | 11/1991 | WIPO ............... | C12N 9/42 |

Primary Examiner—Glenn A. Caldarola
Assistant Examiner—Alexander G. Ghyka
Attorney, Agent, or Firm—Kim William Zerby; T. David Reed; J. J. Yetter

[57] ABSTRACT

The present invention provides a detergent composition comprising a quaternary ammonium compound of formula: $R_1R_2R_3R_4N^+X^-$, wherein $R_1$ is $C_8$–$C_{16}$ alkyl, each of $R_2$, $R_3$ and $R_4$ is independently $C_1$–$C_4$ alkyl or hydroxy alkyl, benzyl or —$(C_2H_4O)_xH$ where x has a value from 2 to 5, not more of $R_2$, $R_3$ or $R_4$ being benzyl, and X is an anion, and a cellulase characterized in that said cellulase provides at least 10% removal of immobilized radio-active labelled carboxymethylcellulose according to the CMC-method at $25\times10^{-6}$% by weight of cellulase protein in the laundry test solution. According to the present invention, a preferred cellulase consists of a homogeneous endoglucanase component which is immunoreactive with a monoclonal antibody raised against a partially purified=43 kD cellulase derived from Humicola insolens DM 1800.

18 Claims, No Drawings

DETERGENT COMPOUNDS WITH HIGH ACTIVITY CELLULASE AND QUATERNARY AMMONIUM COMPOUNDS

This is a continuation of application Ser. No. 08/290,712, filed as PCT/US92/01179 Feb. 15, 1992, published as WO93/16158 Aug. 19, 1993.

TECHNICAL FIELD

The present invention relates to detergent compositions having cleaning and softening benefits.

BACKGROUND OF THE INVENTION

The need for detergent compositions which exhibit not only good cleaning properties, but also good fabric-softening performance, and other fabric care benefits, is well-established in the art.

EP 0 026 529 describes detergent compositions containing smectite-type clays and certain cationic compounds having cleaning and textile softening performance.

The efficiency of cellulolytic enzymes, i.e. cellulases, in terms of textile cleaning and harshness-reducing agent for fabrics has been recognized for some time; GB-A-2,075,028, GB-A-2,095,275 and GB-A-2,094,826, disclose detergent compositions with cellulase for improved cleaning performance; GB-A-1,368,599 discloses the use of cellulase for reducing the harshness of cotton-containing fabrics; U.S. Pat. No. 4,435,307 teaches the use of a cellulolytic enzyme derived from Humicola insolens as well as a fraction thereof, designated ACXI, as a harshness-reducing detergent additive.

EP-A-0 269 168 discloses optimized detergent compositions containing cellulase, which are formulated at a mild alkaline pH range and provide combined fabric cleaning, fabric softening, and fabric care performance. EP-B-0 125 122 discloses a detergent composition which combines cleaning and textile softening performance by using a synergetic mixture of a long-chain tertiary amine and cellulase.

In WO 89109259 have been disclosed cellulase preparations useful for reducing the harshness of cotton-containing fabrics, comprising an endoglucanase component with a high endoase activity and affinity towards cellulose.

The practical exploitation of cellulases has however, been set back by the fact that cellulase preparations such as those disclosed in the above-mentioned prior art documents, are complex mixtures, of which only a certain fraction is effective in the fabric-care context; it was thus difficult to implement cost effective industrial production of cellulase for the detergent industry; and large quantities of such cellulase preparations would need to be applied, in order to obtain the desired effect on fabrics.

Improvements in cellulase production also often have not proven to be sufficiently identifiable in terms of applicability in detergents. Defining a cellulase selection criterium relevant for detergent application of cellulase was made possible by the C14CMC-method disclosed in EP-A-350 098. A minimum of 10% removal of immobilized radioactive labelled carboxymethylcellulose at $25\times10^{-6}\%$ by weight of cellulase protein in the laundry test solution has been found to provide high activity cellulase. A preferred group of cellulase falling under the high activity definition according to the present invention has been disclosed in copending Danish Patent Application No. : 1159/90 filed May 5, 1990. There is disclosed a cellulase preparation consisting essentially of a homogeneous endoglucanase component which is immunoreactive with a monoclonal antibody raised against a partially purified 43 kD cellulase derived from Humicola insolens DM1800.

The finding that this particular endoglucanase component of cellulase is advantageous for the treatment of cellulose-containing materials now permits to produce the cellulase cost-effectively, e.g. by employing recombinant DNA techniques, and allows to apply only a small quantity of the cellulase preparation, and obtain the desired effect on fabrics.

It has surprisingly been found that an improved detergent composition can be formulated which combine superior cleaning and softening performance by using a synergestic mixture of water soluble quaternary ammonium compounds and high active cellulase. Said cellulase having at least 10% CMC removal at $25\times10^{-6}\%$ by weight of cellulase protein in the laundry test solution.

It is another object of the present invention to provide a method for treating fabrics in a washing machine, comprising the utilization of the present detergent compositions, for the main wash cycle.

SUMMARY OF THE INVENTION

The present invention provides a detergent composition comprising a quaternary ammonium compound of formula

$$R_1R_2R_3R_4N^+X^-$$

wherein $R_1$ is $C_8$–$C_{16}$ alkyl, each of $R_2$, $R_3$ and $R_4$ is independently $C_1$–$C_4$ alkyl or hydroxy alkyl, benzyl, or —$(C_2H_{4O})_xH$ where x has a value from 2 to 5, not more than one of $R_2$, $R_3$ or $R_4$ being benzyl, and X is an anion, and a cellulase characterized in that said cellulase provides at least 10% removal of immobilized radio-active labelled carboxymethylcellulose according to the C14 CMC-method at $25\times10^{-6}\%$ by weight of cellulase protein in the laundry test solution.

According to the present invention, a preferred cellulase consists of a homogeneous endoglucanase component which is immunoreactive with a monoclonal antibody raised against a partially purified=43 kD cellulase derived from Humicola insolens DM 1800.

DETAILED DESCRIPTION OF THE INVENTION

Cellulase

The activity of enzymes and particularly the activity of cellulase enzyme has been defined for various applications by different analytical methods. These methods all attempt to provide a realistic assessment of the expected in use performance or at least a measurement correlating with the in use performance. As has been detailed in European Patent Application EP-A-350098, many of the methods, particularly these frequently used by cellulase manufacturers, are not sufficiently correlated with the in use performance of cellulase in laundry detergent compositions. This is due to the various other usage conditions for which these activity measurement methods have been developed.

The method described in EP-A-350098, has been developed to be and to have a predictive correlation for the ranking of cellulase activity in laundry detergent compositions.

The present invention therefore uses the method disclosed in EP-A-350098 to screen cellulases in order to distinguish cellulases which are useful in the present invention and those which would not provide the objectives of the present invention. The screening method, hereinafter referred to as C14CMC-Method, which has been adopted from the method disclosed in EP-A-350098, can be described as follows:

Principle

The principle of the C14CMC-Method for screening is to measure at a defined cellulase concentration in a wash solution the removal of immobilized carboxy methyl cellulose (CMC) from a cloth substrate. The removal of CMC is measured by radio-active labelling of some of the CMC by using C14 radio-active carbon. Simple counting of the amount of radio-active C14 on the cloth substrate before and after the cellulase treatment allows the evaluation of the cellulase activity.

Sample Preparation

CMC preparation: The radio-active CMC stock solution is prepared according to Table I. The radio-active CMC can be obtained by methods referred to in EP-A-350098.

Fabric substrates: The fabric substrates are muslin cotton swatches having a size of 5 cm×5 cm. They are inoculated with 0.35 ml of the radio-active labelled CMC stock solution in their center. The muslin cotton swatches are then airdried.

Immobilization of CMC: To immobilize the radio-active labelled CMC on the muslin cotton swatches, launderometer equipment "Linitest Original Haunau" made by Original Haunau, Germany, is used. A metal jar of the launderometer is filled with 400 ml of hard water (4 mmol/liter of $Ca^{++}$ ions). A maximum number of 13 swatches can be used per jar. The jar is then incubated in a heat-up cycle from 20° C. to 60° C. over 40 minutes in the laundero-meter equipment. After incubation the swatches are rinsed under running city water for 1 minute. They are squeezed and allowed to airdry for at least 30 minutes.

According to EP-A-350098 samples of the swatches with immobilized radio-active CMC can also be measured as "blank samples" without washing.

Sample Treatment

Laundry test solution: The laundry test solution is prepared according to the composition of Table II. It is balanced to pH 7.5. The laundry test solution is the basis to which a cellulase test sample is added. Care should be taken to not dilute the laundry test solution by adding water to a 100% balance prior to having determined the amount of cellulase to be added. The amount of cellulase which is used in this screening test should be added to provide $25 \times 10^{-6}$ weight percent of cellulase protein in the laundry test solution (equivalent to 0.25 milligram/liter at 14.5° C.).

Wash procedure: The swatches thus inoculated with radio-active labelled CMC are then treated in a laundry simulation process. The laundry process is simulated in the launderometer type equipment, "Linitest, Original Haunau", by Original Haunau, Haunau Germany. An individual swatch is put into a 20 cm³ glass vial. The vial is filled with 10 ml of the laundry test solution and then sealed liquid tight. Up to 5 vials are put into each laundero-meter jar. The jar is filled with water as a heat tranfer medium for the laundering simulation. The laundering simulation is conducted as a heat-up cycle from 20° C. to 60° C. over 40 minutes.

After the processing of the samples the vials are submerged in cold water and subsequently each swatch is taken out of its vial, rinsed in a beaker under running soft water, squeezed and allowed to airdry for at least 30 minutes.

Measurement

In order to measure radio-active labelled CMC removal, a scintillation counter, for example, a LKB 1210 Ultrabeta Scintillation Counter, is used. In order to obtain most accurate results, the instruction manual for optimum operation of the particular scintillation counter should be followed. For example, for the LKB 1210 Ultrabeta Scintillation Counter, the following procedure should be followed. The swatch to be measured is put into a plastic vial filled with 12 ml of scintillator liquid (e.g. scintillator 299 from Packard). The swatch is then allowed to stabilize for at least 30 minutes. The vial is then put into the LKB 1210 Ultrabeta Scintillation Counter and the respective radio-activity counts for the swatch is obtained.

In order to measure the amount of CMC removal due only to the cellulase, a measurement of a swatch which has been inocculated at the same time but has been treated in the laundry test solution without cellulase, is necessary. The activity of the cellulase is then expressed as percent of radio-active labelled CMC removal. This percentage is calculated by the following formula:

$$\% \text{ of radio-active } CMC \text{ removal} = \frac{XO - XC}{XO} \times 100$$

Wherein

XO is the radioactivity scintillation count of a swatch treated with the laundry test solution without cellulase XC is the radioactivity scintillation count of a swatch treated with the laundry test solution containing the cellulase to be evaluated Statistical Considerations, Procedure Confirmation In order to provide statistically sound results, standard statistical analysis should be employed. For the given example, using the LKB 1210 Ultrabeta Scintillation Counter, it has been found that a sample size of 3 swatches for each radioactivity scintillation count can be used.

In order to confirm the procedure by internal crosschecking, measurement and calculation of the "blank sample" according to EP-A-350098 are recommended. This will allow to detect and eliminate errors.

Interpretation of results

The described screening test does provide a fast, unique and reliable method to identify cellulases which satisfy the activity criteria of the present invention versus cellulases which are not part of the present invention.

It has been found that a removal of 10% or more of the immobilized radioactive labelled CMC according to the above C14CMC-method, indicates that the respective cellulase satisfies the requirements of the invention.

It will be obvious to those skilled in the art that removal percentages above 10% indicate a higher activity for the respective cellulase. It therefore is contemplated that cellulase providing above 25% or preferably above 50% removal of radioactive labelled CMC, at the protein concentration in the laundry test solution according to the C14CMC-method, would provide indication of an even better performance of the cellulase for use in laundry detergents.

It also has been contemplated that usage of higher concentrations of cellulase for C14CMC-method, would provide higher removal percentages. However, there exists no linear proven correlation between cellulase concentration and removal percentage obtained by it.

It also has been contemplated that usage of higher concentrations of cellulase for C14CMC-method, would provide higher removal percentages.

TABLE I

Radioactive $C_{14}$ labelled CMC stock solution
(all percentages by weight of total solution)

| | |
|---|---|
| Total CMC* (CMC should be detergent grade CMC with a degree of substitution from about 0.47 to about 0.7) | $99.2 \times 10^{-3}\%$ |
| Ethanol | $14985.12 \times 10^{-3}\%$ |
| Deionized Water | $84915.68 \times 10^{-3}\%$ |
| Total: | 100% |

*Total CMC contains non-radio-active and radio-active CMC to provide a radio-activity which allows sufficiently clear readings on the scintillation counter used. For example, the radio-active CMC can have an activity of 0.7 millicurie/g and be mixed with non-radio-active CMC at a ratio of 1:6.7.

TABLE II

Laundry test solution
(all percentages by weight of total solution)

| | |
|---|---|
| Linear $C_{12}$ alkyl benzene sulphonic acid | 0.110% |
| Coconut alkyl sulphate (TEA salt) | 0.040% |
| $C_{12-15}$ alcohol ethoxylate (EO7) | 0.100% |
| Coconut fatty acid | 0.100% |
| Oleic acid | 0.050% |
| Citric acid | 0.010% |
| Triethanolamine | 0.040% |
| Ethanol | 0.060% |
| Propanediol | 0.015% |
| Sodium hydroxide | 0.030% |
| Sodium formate | 0.010% |
| Protease | 0.006% |
| Water (2.5 mmol/liter $Ca^{++}$), pH adjustment agent (HCL or NAOH solutions) and cellulase | balance to 100% |

The Water-Soluble Quaternary Ammonium Compound

The water-soluble soluble quaternary ammonium compound has the formula:

$$R_1R_2R_3R_4N^+X^-$$

wherein $R_1$ is $C_8$–$C_{16}$ alkyl, each of $R_2$, $R_3$ and $R_4$ is independently $C_1$–$C_4$ alkyl, $C_1$–$C_4$ hydroxy alkyl, benzyl, and $—(C_2H_{4O})_xH$ where x has a value from 2 to 5, and X is an anion. Not more than one of $R_2$, $R_3$ or $R_4$ should be benzyl.

The preferred alkyl chain length for $R_1$ is $C_{12}$–$C_{15}$ particularly where the alkyl group is a mixture of chain lengths derived from coconut or palm kernel fat or is derived synthetically by olefin build up or OXO alcohols synthesis. Preferred groups for $R_2R_3$ and $R_4$ are methyl and hydroxyethyl groups and the anion X may be selected from halide, methosulphate, acetate and phosphate ions. Examples of suitable quaternary ammonium compounds are coconut trimethyl ammonium bromide
coconut methyl dihydroxyethyl ammonium bromide
decyl triethyl ammonium chloride
decyl dimethyl hydroxyethyl ammonium bromide
myristyl trimethyl ammonium methyl sulphate
lauryl dimethyl benzyl ammonium bromide
lauryl methyl (ethenoxy)$_4$ ammonium bromide The water-soluble cationic component of the compositions of the present invention is capable of existing in cationic form in a 0.1% aqueous solution at pH 10. The water-soluble cationic compound will normally be present in an amount of from 0.2% to 10% by weight of the detergent composition.

Detergent Adjuncts

The detergent compositions of the present invention include components that are usually found in laundry detergents, these components being present in an amount of up to 95% by weight of the composition.

These include nonionic and zwitterionic surfactants, builder salts, bleaching agents and organic precursors therefor, suds suppression agents, soil suspending and anti-redeposition agents, enzymes, optical brighteners colouring agents and perfumes.

A wide range of anionic surfactants can be used in the compositions of the present invention.

Suitable anionic non-soap surfactants are water soluble salts of alkyl benzene sulfonates, alkyl sulfates, alkyl polyethoxy ether sulfates, paraffin sulfonates, alphaolefin sulfonates, alpha-sulfocarboxylates and their esters, alkyl glyceryl ether sulfonates, fatty acid monoglyceride sulfates and sulfonates, alkyl phenol polyethoxy ether sulfates, 2-acdylozy-alkane-1-sulfonates, and beta-alkoxy alkane sulfonates. Soaps are also suitable anionic surfactants.

Especially preferred alkyl benzene sulfonates have 9 to 15 carbon atoms in a linear or branched alkyl chain, more especially 11 to 13 carbon atoms. Suitable alkyl sulfates have 10 to 22 carbon atoms in the alkyl chain, more especially from 12 to 18 carbon atoms. Suitable alkyl polyethoxy ether sulfates have 10 to 18 carbon atoms in the alkyl chain and have an average of 1 to 12 —$CH_2CH_2O$— groups per molecule, especially 10 to 16 carbon atoms in the alkyl chain and an average of 1 to 6 —$CH_2CH_2O$— groups per molecule.

Suitable paraffin sulfonates are essentially linear and contain from 8 to 24 carbon atoms, more especially from 14 to 18 carbon atoms. Suitable alphaolefin sulfonates have 10 to 24 carbon atoms, more especially 14 to 16 carbon atoms; alphaolefin sulfonates can be made by reaction with sulfur trioxide followed by neutralization under conditions such that any sultones present are hydrolyzed to the corresponding hydroxy alkane sulfonates. Suitable alphasulfocarboxylates contain from 6 to 20 carbon atoms; included herein are not only the salts of alphasulfonated fatty acids but also their esters made from alcohols containing 1 to 14 carbon atoms.

Suitable alkyl glyceryl ether sulfates are ethers of alcohols having 10 to 18 carbon atoms, more especially those derived from coconut oil and tallow.

Suitable alkyl phenol polyethoxy ether sulfates have 8 to 12 carbon atoms in the alkyl chain and an average of 1 to 6 —CH2CH20— groups per molecule. Suitable 2-acyloxy-alkane-1-sulfonates contain from 2 to 9 carbon atoms in the acyl group and 9 to 23 carbon atoms in the alkane moiety. Suitable beta-alkyloxy alkane sulfonates contain 1 to 3 carbon atoms in the alkyl group and 8 to 20 carbon atoms in the alkane moiety.

The alkyl chains of the foregoing non-soap anionic surfactants can be derived from natural sources such as coconut oil or tallow, or can be made synthetically as for example using the Ziegler or Oxo processes. Water solubility can be achieved by using alkali metal, ammonium, or alkanolammonium cations; sodium is preferred. Mixtures of anionic surfactants are contemplated by this invention; a satisfactory mixture contains alkyl benzene sulfonate having 11 to 13 carbon atoms in the alkyl group and alkyl sulfate having 12 to 18 carbon atoms in the alkyl group.

Suitable soaps contain 8 to 18 carbon atoms, more especially 12 to 18 carbon atoms. Soaps can be made by direct saponification of natural fats and oils such as coconut oil, tallow and palm oil, or by the neutralization of free fatty acids obtained from either natural or synthetic sources. The soap cation can be alkali metal, ammonium or alkanolammonium, sodium is preferred.

The compositions contain from 3 to 40% of anionic detergent, preferably from 4 to 15% of anionic detergent, more preferably, 5–10% of anionic surfactant.

As stated previously, the compositions of the present invention combine good softening and cleaning performance and in order to maintain the latter it is essential that the overall surfactant character be anionic. The molar ratio of the water-soluble quaternary ammonium compound to the anionic surfactant component should therefore be less than 1:1 and desirably should be less than 1:1.5. In preferred embodiments of the invention such as heavy duty laundry detergent formulations, the molar ratio should be less than 1:2.

Subject to these constraints the cationic compound will normally be present in an amount of from 0.5% to 15% by weight of the composition, preferably from 1% to 5% and most preferably from 1.5% to 3% by weight.

Nonionic and zwitterionic surfactants may be incorporated in amounts of up to 50% by weight of the total surfactant but normally are present in amounts of less than 30% of the total surfactant. By "total surfactant" is meant the sum of the anionic surfactant (a) cationic component (b) and any added nonionic and/or zwitterionic surfactant. The incorporation of 15–25% nonionic surfactant based on the total surfactant weight (corresponding to 1–2% on a total composition basis) has been found to provide advantages in the removal of oily soils. Suitable nonionics are water soluble ethoxylated materials of HLB 11.5–177.0 and include (but are not limited to) $C_{10}$–$C_{20}$ primary and secondary alcohol ethoxy ethoxylates and $C_6$–$C_{10}$ alkylphenol ethoxylates. $C_{14}$–$C_{18}$ linear primary alcohols condensed with from seven to thirty moles of ethylene oxide per mole of alcohol are preferred, examples being $C_{14}$–$C_{15}$ (EO)7, $C_{16}$–$C_{18}$ (EO) 25 and especially $C_{16}$–$C_{18}$ (EO) 11.

Suitable zwitterionic surfactants include the $C_{12}$–$C_{16}$ alkyl betaines and sultaines. These and other zwitterionic and nonionic surfactants are disclosed in Laughlin & Heuring U.S. Pat. No. 3,929,678.

Detergent builder can be inorganic or organic in character. Non limiting examples of suitable water-soluble, inorganic alkaline detergent builder salts include the alkali metal carbonates, borates, phosphates, polyphosphates, bicarbonates, and silicates. Specific examples of such salts include the sodium and potassium tetraborates, bicarbonates, carbonates, tripolyphosphates, pyrophosphates, penta-polyphosphates and hexametaphosphates. Sulphates are usually also present.

Preferred water soluble builders are sodium tripolyphosphate and sodium silicate, and usually both are present. In particular, it is preferred that a substantial proportion, for instance for 3% to 15% by weight of the composition of sodium silicate (solids) or ratio (weights ratio $SiO_2$:$Na_2O$ from 1:1 to 3.5:1 be employed.

A further class of detergency builder materials useful in the present invention are insoluble sodium alumino silicates of the formula:

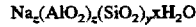
$Na_z(AlO_2)_z(SiO_2)_y.xH_2O$ wherein z and y are integers equal to at least 6, the molar ratio of z to y is in the range of from 1.0:1 to 0.5:1 and x is an integer from 15 to 264. A preferred material is $Na_{12}(SiO_2AlO_2)_{12}27H_2O$. If present, incorporation of 5% to 25% by weight of aluminosilicate is suitable, partially replacing water-soluble builder salts, provided that sufficient water-soluble alkaline salts remain to provide the specified pH of the composition in aqueous solution.

Detergency builder salts are normally included in amounts of from 10% to 80% by weight of the composition preferably from 20% to 70% and most usually from 30% to 60% by weight.

Bleaching agents, suds controlling agents, soil suspending agents, proteolytic, amylolytic or lipolytic enzymes, especially proteolytic, and optical brighteners, may be present.

Colours, non-substantive, and perfumes, as required to improve the aesthetic acceptability of the product, are usually incorporated.

The detergent compositions according to the invention can be in liquid, paste or granular forms. Granular compositions according to the present invention can also be in "compact form", i.e. they may have a relatively higher density than conventional granular detergent compositions according to the present invention will contain a lower amount of "inorganic filler salt", compared to conventional granular detergents; typical filler salts are alkaline earth metal salts of sulphates and chlorides, typically sodium sulphate; "compact" detergents typically comprise not more than 10% filler salt.

PREPARATION OF THE COMPOSITIONS

The detergent compositions may be prepared in any way, as appropriate to their physical form, as by mixing the components, co-agglomerating them or dispersing them in a liquid carrier. In granular form a detergent salt builder can be incorporated and the granular is prepared by spray drying an aqueous slurry of the non-heat-sensitive components, and the builder salt to form spray dried granules into which may be admixed the heat sensitive components such as persalts, enzymes, perfumes. The water-soluble quaternary compound may be included in the slurry for spray drying or it may be incorporated by dissolving or dispersing the cationic component in water or another suitable volatile liquid and then spraying this solution of disperion onto the spray dried granules before or after other heat sensitive solids have been dry mixed with them. Alternatively the water-soluble quaternary compound can be dry mixed together with the other heat sensitive solids. Clay components may be added to the slurry for spray drying or may be dry mixed, as preferred for reasons unrelated to its softening effect, such as for optimum colour of the product.

The invention is illustrated by the following non-limiting examples.

The following examples are meant to exemplify compositions of the present invention, but are not necessarily meant to limit or otherwise define the scope of the invention, said scope being determined according to claims which follow.

EXAMPLE I

Criticality of the Cellulase Performance Parameter of Claim 1

The following test was conducted:
Test conditions
Washing temperature: 60° C. (heat up cycle)
Washing time: 40 min.
pH=7.5

Water hardness: 4 mmol/L
Detergent concentration: 1%
Detergent composition: crf. EPA 350 098 ex. 1
Cellulases:
  1) Celluzyme$^R$ supplied by Novo Nordisk=reference
  2) 43 kD endoglucanase=cellulase according to the invention Test Results

|  | % C14-CMC Removal by Cellulase |
|---|---|
| Detergent without cellulase (= reference) | 0 |
| Detergent + Celluzyme$^R$ | |
| 1.5 mg protein/L (150 × 10$^{-6}$%) | 12.7 |
| 3.0 mg protein/L (300 × 10$^{-6}$%) | 17.7 |
| 4.5 mg protein/L (450 × 10$^{-6}$%) | 21.5 |
| Detergent + 43kD endoglucanase | |
| 0.3 mg protein/L (30 × 10$^{-6}$%) | 20.3 |

Discussion of the Results

The above data clearly demonstrate the criticality of the claimed parameter for the cellulases of the invention over the commercially available Celluzyme.

EXAMPLE II

Two sets of different detergent compositions are prepared, all based on a compact granular detergent composition.

Such a compact granular detergent composition typically contains the following ingredients:

| Linear alkyl benzene sulphonate (LAS) | 9.5% |
|---|---|
| Alkyl suphate | 3% |
| Nonionic | 4% |
| Trisodium citrate | 21% |
| Zeolite | 33% |
| Citric acid | 6% |
| Polymer | 4% |
| Chelant | 0.2% |
| Sodium sulphate | 6% |
| Sodium silicate | 2% |
| Perborate | 0.5% |
| Phenol sulphonate | 0.1% |

The above detergent composition was supplemented as indicated below:

SET 1: With 43kD endoglucanase

| (*)Quaternary ammonium compounds level mg/l | No Cellulase (PSU) | 2.4 mg Cellulase/ L wash liquor (240 × 10$^{-6}$%) (PSU) |
|---|---|---|
| 0 | −2.5 | 0 |
| 100 | −2.5 | 1.5 |
| 200 | −2.5 | 3.5 |

SET 2: With Celluzyme$^R$

| (*)Quaternary ammonium compounds level mg/l | No Cellulase (PSU) | 92 mg Cellulase/ L wash liquor (9200 × 10$^{-6}$%) (PSU) |
|---|---|---|
| 0 | −0.3 | 0 |
| 100 | −0.3 | 0 |
| 200 | −0.3 | 0 |

(*)$C_{12}$–$C_{14}$ dimethyl (hydroxyethyl) ammonium chloride

Test procedure

Cellulase has the property to de-pill worn cotton fabrics. In a model test the measurement of de-pilling is used to assess cellulase performance. Swatches of worn blue pyjama fabric were treated with different wash solutions in a Laundrometer (temperature 30° C.). The water hardness was 2.5 mM Calcium. After tumble drying, the fabrics were graded for de-pilling by direct comparison of the different detergent matrices. Visual grading was performed by expert judges using a 0 to 4 scale (PSU). In this scale 0 is fiven for no difference and 4 is given for maximum difference. The PSU grading are statistical recount, an average of 4 replicates is made, LSD (least significant difference) is 0.5 PSU at 95% confidence level.

The above results demonstrate the synergy between the quaternary ammonium compound and the 43 kD cellulase in that the performance of the 43 kD cellulase is significantly improved by the quaternary ammonium compound.

EXAMPLE III–VI

Test procedure 3.5 kg of clean fabric laundry loads were washed in an automatic drum washing machine Miele 423 at 60° C. The hardness of the water was 2.5 mM Calcium and the composition concentration was 0.7% in the wash liquor. For softness evaluation swatches of terry towel were line dried prior for assessment of softness. Comparative softness assessment was done by expert judges using a scale of 0 to 4 panel-score-units (PSU). In this scale 0 is given for no difference and 4 is given for maximum difference. Softness was assessed after one and after one, four and eight wash cycles. LSD is 0.5 psu at the 95% confidence level. The following compositions are made:

| | Percentage by weight | | | |
|---|---|---|---|---|
| Ingredients | III | IV | V | VI |
| Surfactant | | | | |
| Linear alkylbenzene sulfonate | 8 | 8 | 8 | 8 |
| Tallow alkyl sulphate | 2 | 2 | 2 | 2 |
| $C_{12}$–$C_{14}$ dimeth. hydroxyeth ammonium chlo | 5 | — | 5 | — |
| Fatty alcohol ($C_{12}$–$C_{15}$) ethoxylate | 1.5 | 1.5 | 1.5 | 1.5 |
| Builder/chelants | | | | |
| Zeolite A | 18.5 | 18.5 | 18.5 | 18.5 |
| Copolymer of maleic and acrylic acid, sodium salt | 5 | 5 | 5 | 5 |
| Bleach | | | | |
| Sodium perborate | 11 | 11 | 11 | 11 |
| N,N,N,T-Tetraacetyl ethylene diamine | 4 | 4 | 4 | 4 |
| Perfume | 0.5 | 0.5 | 0.5 | 0.5 |
| Enzymes | — | — | — | — |
| Protease | 1.6 | 1.6 | 1.6 | 1.6 |
| Cellulase 43 kD | 0.5 | 0.5 | — | — |
| Softness system | | | | |
| Smectite/montmorillonite clays | 12.5 | 12.5 | 12.5 | 12.5 |
| Polyethylene oxide | 0.3 | 0.3 | 0.3 | 0.3 |
| Buffer | | | | |
| Carbonate | 10.6 | 10.6 | 10.6 | 10.6 |
| Silicate (2.0) | 4 | 4 | 4 | 4 |
| CMC, chelants Admix and spray-on (suds suppression, miscellaneous, . . . ) | balance to 100 | | | |

Results

Detergent composition III 0.5% (=40×10$^{-6}$% mg proteine wash liquor) 43 kD cellulase+5% quaternary ammonium component versus detergent composition IV 0.5% (=40×10⁻⁶% mg proteine wash liquor) 43 kD cellulase no quaternary ammonium component

| Cycles | 1 | 4 | 8 |
|---|---|---|---|
| PSU | 0 | 0.8s | 1.8s |

Detergent composition V+5% quaternary ammonium composition versus detergent composition VI no quaternary ammonium component

| Cycles | 1 | 4 | 8 |
|---|---|---|---|
| PSU | — | — | 0.1 | significant difference at 95% confidence

Conclusion

The above results demonstate that the quaternary ammonium compound/43 kD cellulase combination gives a statistical significant better performance than the sum of the individual actions of both ingredients.

Formulation Examples

The following compositions are made:

| Ingredients | Composition (% by weight) Regular products | | | |
|---|---|---|---|---|
| | I | II | III | IV |
| $C_{11-12}$ alkyl benzene sulfonate | 7 | 5 | 4 | — |
| Tallow alcohol sulfate (Na) | — | 2 | — | — |
| $C_{14-15}$ alkyl sulfate (Na) | — | — | 3 | 4 |
| A-Olefin ($C_{12-18}$) sulfonate (Na) | — | — | — | 0.5 |
| Tallow alcohol ethoxylate ($EO_{11}$) | 0.5 | — | — | — |
| Fatty alcohol ($C_{12-15}$) ethoxylate ($EO_7$) | — | — | — | 0.5 |
| Hydrogenated tallow fatty acid | — | 0.5 | — | — |
| $C_{12-14}$ Dimethyl (hydroethyl) ammonium chloride | — | — | 5 | 5 |
| Sodium tripolyphosphate | 24 | — | — | 25 |
| Zeolite A | — | 20 | 20 | — |
| Sodium citrate | — | 5 | 5 | — |
| Oleic fatty acid | — | — | — | — |
| Citric acid | — | — | — | — |
| $C_{14-16}$ alkyl succinate | — | — | — | — |
| 1,2-Propanediol | — | — | — | — |
| Ethanol | — | — | — | — |
| Na Metaborate Octahydrate | — | — | — | — |
| Polyethylene oxide 5 MM molecular weight | 0.05 | — | — | 0.05 |
| Polyethylene oxide 0.3 MM molecular weight | — | 0.3 | — | — |
| Sodium sulfate | 12 | 10 | 15 | 5 |
| Sodium carbonate | 5 | 7 | — | 15 |
| Sodium silicate | 4 | 4 | 4 | 4 |
| Sodium perborate (1 aq.) | 15 | 15 | 18 | 15 |
| N,N,N,N-Tetraacetylethylene diamine | 3 | 3 | — | 3 |
| CMC | 0.3 | 0.3 | 0.3 | 0.3 |
| Polyacrylate (MW 1000–20 000) | — | 1.5 | — | — |
| Polyacrylate (MW 4000–5000) | — | — | 3 | — |
| Maleic-acrylic copolymer | 2 | — | — | 3 |
| Cellulase | 0.5 | 0.5 | 0.5 | 1 |
| Smectite/montmorillonite clay | 10.5 | 10.5 | 10.5 | 10.5 |

| | | | | 0.3 |
|---|---|---|---|---|
| Phosphate | — | — | — | 0.3 |
| Admix and spray-on (perfumes, protease, amylase, lipolase, buffer, sud suppression, miscelaneous, moisture and minors) | | balance to 100 | | |

| Ingredients | Composition (% by weight) | | |
|---|---|---|---|
| | Compact product | | Liquid product |
| | I | II | I |
| $C_{11-12}$ alkyl benzene sulfonate | 8 | — | 10 |
| Tallow alcohol sulfate (Na) | 2 | 2 | — |
| $C_{14-15}$ alkyl sulfate (Na) | — | 6 | 1 |
| A-Olefin ($C_{12-18}$) sulfonate (Na) | — | — | — |
| Tallow alcohol ethoxylate ($EO_{11}$) | — | — | — |
| Fatty alcohol ($C_{12-15}$) ethoxylate ($EO_7$) | — | — | — |
| Hydrogenated tallow fatty acid | — | — | — |
| $C_{12-14}$ Dimethyl (hydroethyl) ammonium chloride | 5 | 5 | — |
| Sodium tripolyphosphate | — | — | — |
| Zeolite A | 15 | 19 | — |
| Sodium citrate | — | 6 | — |
| Oleic fatty acid | — | — | 1 |
| Citric acid | — | — | 2 |
| $C_{14-16}$ alkyl succinate | — | — | 10 |
| 1,2-Propanediol | — | — | 3 |
| Ethanol | — | — | 7 |
| Na Metaborate Octahydrate | — | — | 1 |
| Polyethylene oxide 5 MM molecular weight | — | — | — |
| Polyethylene oxide 0.3 MM molecular weight | 0.3 | 0.3 | — |
| sulfonate | — | 2 | — |
| Sodium carbonate | 11 | 11 | — |
| Sodium silicate | 4 | 3 | — |
| Sodium perborate (1 aq.) | 11 | 12 | — |
| N,N,N,N-Tetraacetylethylene diamine | 4 | 3 | — |
| CMC | 0.4 | 0.3 | — |
| Polyacrylate (MW 1000–20 000) | — | — | — |
| Polyacrylate (MW 4000–5000) | — | — | — |
| Maleic-acrylic copolymer | 5 | 4 | — |
| Cellulase | 1 | 0.5 | 1 |
| Smectite/montmorillonite clay | 12 | 12 | 10.5 |
| Layered silicate | 7 | — | — |
| Admix and spray-on (perfumes, protease, amylase, lipolase, buffer, sud suppression, miscelaneous, moisture and minors) | | balance to 100 | |

SEQUENCE DESCRIPTION:

```
GGATCCAAG ATG CGT TCC TCC CCC CTC CTC CCG TCC GCC GTT GTG GCC        48
          Met Arg Ser Ser Pro Leu Leu Pro Ser Ala Val Val Ala
          -21 -20                  -15                 -10

GCC CTG CCG GTG TTG GCC CTT GCC GCT GAT GGC AGG TCC ACC CGC TAC      96
Ala Leu Pro Val Leu Ala Leu Ala Ala Asp Gly Arg Ser Thr Arg Tyr
            -5                   1               5
```

SEQUENCE DESCRIPTION:

```
TGG GAC TGC TGC AAG CCT TCG TGC GGC TGG GCC AAG AAG GCT CCC GTG      144
Trp Asp Cys Cys Lys Pro Ser Cys Gly Trp Ala Lys Lys Ala Pro Val
    10              15                  20

AAC CAG CCT GTC TTT TCC TGC AAC GCC AAC TTC CAG CGT ATC ACG GAC      192
Asn Gln Pro Val Phe Ser Cys Asn Ala Asn Phe Gln Arg Ile Thr Asp
25              30                  35                          40

TTC GAC GCC AAG TCC GGC TGC GAG CCG GGC GGT GTC GCC TAC TCG TGC      240
Phe Asp Ala Lys Ser Gly Cys Glu Pro Gly Gly Val Ala Tyr Ser Cys
                45                  50                  55

GCC GAC CAG ACC CCA TGG GCT GTG AAC GAC GAC TTC GCG CTC GGT TTT      288
Ala Asp Gln Thr Pro Trp Ala Val Asn Asp Asp Phe Ala Leu Gly Phe
            60                  65                  70

GCT GCC ACC TCT ATT GCC GGC AGC AAT GAG GCG GGC TGG TGC TGC GCC      336
Ala Ala Thr Ser Ile Ala Gly Ser Asn Glu Ala Gly Trp Cys Cys Ala
        75                  80                  85

TGC TAC GAG CTC ACC TTC ACA TCC GGT CCT GTT GCT GGC AAG AAG ATG      384
Cys Tyr Glu Leu Thr Phe Thr Ser Gly Pro Val Ala Gly Lys Lys Met
    90                  95                  100

GTC GTC CAG TCC ACC AGC ACT GGC GGT GAT CTT GGC AGC AAC CAC TTC      432
Val Val Gln Ser Thr Ser Thr Gly Gly Asp Leu Gly Ser Asn His Phe
105             110                 115                 120

GAT CTC AAC ATC CCC GGC GGC GGC GTC GGC ATC TTC GAC GGA TGC ACT      480
Asp Leu Asn Ile Pro Gly Gly Gly Val Gly Ile Phe Asp Gly Cys Thr
                125                 130                 135

CCC CAG TTC GGC GGT CTG CCC GGC CAG CGC TAC GGC GGC ATC TCG TCC      528
Pro Gln Phe Gly Gly Leu Pro Gly Gln Arg Tyr Gly Gly Ile Ser Ser
            140                 145                 150

CGC AAC GAG TGC GAT CGG TTC CCC GAC GCC CTC AAG CCC GGC TGC TAC      576
Arg Asn Glu Cys Asp Arg Phe Pro Asp Ala Leu Lys Pro Gly Cys Tyr
        155                 160                 165

TGG CGC TTC GAC TGG TTC AAG AAC GCC GAC AAT CCG AGC TTC AGC TTC      624
Trp Arg Phe Asp Trp Phe Lys Asn Ala Asp Asn Pro Ser Phe Ser Phe
    170                 175                 180

CGT CAG GTC CAG TGC CCA GCC GAG CTC GTC GCT CGC ACC GGA TGC CGC      672
Arg Gln Val Gln Cys Pro Ala Glu Leu Val Ala Arg Thr Gly Cys Arg
185                 190                 195                 200

CGC AAC GAC GAC GGC AAC TTC CCT GCC GTC CAG ATC CCC TCC AGC AGC      720
Arg Asn Asp Asp Gly Asn Phe Pro Ala Val Gln Ile Pro Ser Ser Ser
                205                 210                 215

ACC AGC TCT CCG GTC AAC CAG CCT ACC AGC ACC AGC ACC ACG TCC ACC      768
Thr Ser Ser Pro Val Asn Gln Pro Thr Ser Thr Ser Thr Thr Ser Thr
            220                 225                 230

TCC ACC ACC TCG AGC CCG CCA GTC CAG CCT ACG ACT CCC AGC GGC TGC      816
Ser Thr Thr Ser Ser Pro Pro Val Gln Pro Thr Thr Pro Ser Gly Cys
        235                 240                 245

ACT GCT GAG AGG TGG GCT CAG TGC GGC GGC AAT GGC TGG AGC GGC TGC      864
Thr Ala Glu Arg Trp Ala Gln Cys Gly Gly Asn Gly Trp Ser Gly Cys
    250                 255                 260

ACC ACC TGC GTC GCT GGC AGC ACT TGC ACG AAG ATT AAT GAC TGG TAC      912
Thr Thr Cys Val Ala Gly Ser Thr Cys Thr Lys Ile Asn Asp Trp Tyr
265                 270                 275                 280

CAT CAG TGC CTG TAGACGCAGG GCAGCTTGAG GGCCTTACTG GTGGCCGCAA          964
His Gln Cys Leu
            285

CGAAATGACA CTCCCAATCA CTGTATTAGT TCTTGTACAT AATTTCGTCA TCCCTCCAGG   1024

GATTGTCACA TAAATGCAAT GAGGAACAAT GAGTAC                             1060

Met Arg Ser Ser Pro Leu Leu Pro Ser Ala Val Val Ala Ala Leu Pro
-21 -20              -15                 -10
```

-continued

SEQUENCE DESCRIPTION:

| Val -5 | Leu | Ala | Leu | Ala | Ala 1 | Asp | Gly | Arg | Ser 5 | Thr | Arg | Tyr | Trp | Asp 10 | Cys |
|---|---|---|---|---|---|---|---|---|---|---|---|---|---|---|---|
| Cys | Lys | Pro | Ser 15 | Cys | Gly | Trp | Ala | Lys 20 | Lys | Ala | Pro | Val | Asn 25 | Gln | Pro |
| Val | Phe | Ser 30 | Cys | Asn | Ala | Asn | Phe 35 | Gln | Arg | Ile | Thr | Asp 40 | Phe | Asp | Ala |
| Lys | Ser 45 | Gly | Cys | Glu | Pro | Gly 50 | Gly | Val | Ala | Tyr | Ser 55 | Cys | Ala | Asp | Gln |
| Thr 60 | Pro | Trp | Ala | Val | Asn 65 | Asp | Asp | Phe | Ala | Leu 70 | Gly | Phe | Ala | Ala | Thr 75 |
| Ser | Ile | Ala | Gly | Ser 80 | Asn | Glu | Ala | Gly | Trp 85 | Cys | Cys | Ala | Cys | Tyr 90 | Glu |
| Leu | Thr | Phe | Thr 95 | Ser | Gly | Pro | Val | Ala 100 | Gly | Lys | Lys | Met | Val 105 | Val | Gln |
| Ser | Thr | Ser 110 | Thr | Gly | Gly | Asp | Leu 115 | Gly | Ser | Asn | His | Phe 120 | Asp | Leu | Asn |
| Ile | Pro 125 | Gly | Gly | Gly | Val | Gly 130 | Ile | Phe | Asp | Gly | Cys 135 | Thr | Pro | Gln | Phe |
| Gly 140 | Gly | Leu | Pro | Gly | Gln 145 | Arg | Tyr | Gly | Gly | Ile 150 | Ser | Ser | Arg | Asn | Glu 155 |
| Cys | Asp | Arg | Phe | Pro 160 | Asp | Ala | Leu | Lys | Pro 165 | Gly | Cys | Tyr | Trp | Arg 170 | Phe |
| Asp | Trp | Phe | Lys 175 | Asn | Ala | Asp | Asn | Pro 180 | Ser | Phe | Ser | Phe | Arg 185 | Gln | Val |
| Gln | Cys | Pro 190 | Ala | Glu | Leu | Val | Ala 195 | Arg | Thr | Gly | Cys | Arg 200 | Arg | Asn | Asp |
| Asp | Gly 205 | Asn | Phe | Pro | Ala | Val 210 | Gln | Ile | Pro | Ser | Ser 215 | Ser | Thr | Ser | Ser |
| Pro 220 | Val | Asn | Gln | Pro | Thr 225 | Ser | Thr | Ser | Thr | Thr 230 | Ser | Thr | Ser | Thr | Thr 235 |
| Ser | Ser | Pro | Pro | Val 240 | Gln | Pro | Thr | Thr | Pro 245 | Ser | Gly | Cys | Thr | Ala 250 | Glu |
| Arg | Trp | Ala | Gln 255 | Cys | Gly | Gly | Asn | Gly 260 | Trp | Ser | Gly | Cys | Thr 265 | Thr | Cys |
| Val | Ala | Gly 270 | Ser | Thr | Cys | Thr | Lys 275 | Ile | Asn | Asp | Trp | Tyr 280 | His | Gln | Cys |
| Leu | | | | | | | | | | | | | | | |

```
GAATTCGCGG CCGCTCATTC ACTTCATTCA TTCTTTAGAA TTACATACAC TCTCTTTCAA    60

AACAGTCACT CTTTAAACAA AACAACTTTT GCAACA ATG CGA TCT TAC ACT CTT     114
                                       Met Arg Ser Tyr Thr Leu
                                        1               5

CTC GCC CTG GCC GGC CCT CTC GCC GTG AGT GCT GCT TCT GGA AGC GGT     162
Leu Ala Leu Ala Gly Pro Leu Ala Val Ser Ala Ala Ser Gly Ser Gly
         10                  15                  20

CAC TCT ACT CGA TAC TGG GAT TGC TGC AAG CCT TCT TGC TCT TGG AGC     210
His Ser Thr Arg Tyr Trp Asp Cys Cys Lys Pro Ser Cys Ser Trp Ser
         25                  30                  35

GGA AAG GCT GCT GTC AAC GCC CCT GCT TTA ACT TGT GAT AAG AAC GAC     258
Gly Lys Ala Ala Val Asn Ala Pro Ala Leu Thr Cys Asp Lys Asn Asp
     40                  45                  50

AAC CCC ATT TCC AAC ACC AAT GCT GTC AAC GGT TGT GAG GGT GGT GGT     306
Asn Pro Ile Ser Asn Thr Asn Ala Val Asn Gly Cys Glu Gly Gly Gly
55                   60                  65                  70

TCT GCT TAT GCT TGC ACC AAC TAC TCT CCC TGG GCT GTC AAC GAT GAG     354
Ser Ala Tyr Ala Cys Thr Asn Tyr Ser Pro Trp Ala Val Asn Asp Glu
                 75                  80                  85
```

SEQUENCE DESCRIPTION:

| | | | | | | | | | | | | | | | | |
|---|---|---|---|---|---|---|---|---|---|---|---|---|---|---|---|---|
| CTT | GCC | TAC | GGT | TTC | GCT | GCT | ACC | AAG | ATC | TCC | GGT | GGC | TCC | GAG | GCC | 402 |
| Leu | Ala | Tyr | Gly 90 | Phe | Ala | Ala | Thr | Lys 95 | Ile | Ser | Gly | Gly | Ser 100 | Glu | Ala | |
| AGC | TGG | TGC | TGT | GCT | TGC | TAT | GCT | TTG | ACC | TTC | ACC | ACT | GGC | CCC | GTC | 450 |
| Ser | Trp | Cys 105 | Cys | Ala | Cys | Tyr | Ala | Leu 110 | Thr | Phe | Thr | Thr 115 | Gly | Pro | Val | |
| AAG | GGC | AAG | AAG | ATG | ATC | GTC | CAG | TCC | ACC | AAC | ACT | GGA | GGT | GAT | CTC | 498 |
| Lys | Gly 120 | Lys | Lys | Met | Ile | Val 125 | Gln | Ser | Thr | Asn | Thr 130 | Gly | Gly | Asp | Leu | |
| GGC | GAC | AAC | CAC | TTC | GAT | CTC | ATG | ATG | CCC | GGC | GGT | GGT | GTC | GGT | ATC | 546 |
| Gly 135 | Asp | Asn | His | Phe | Asp 140 | Leu | Met | Met | Pro | Gly 145 | Gly | Gly | Val | Gly | Ile 150 | |
| TTC | GAC | GGC | TGC | ACC | TCT | GAG | TTC | GGC | AAG | GCT | CTC | GGC | GGT | GCC | CAG | 594 |
| Phe | Asp | Gly | Cys | Thr 155 | Ser | Glu | Phe | Gly | Lys 160 | Ala | Leu | Gly | Gly | Ala 165 | Gln | |
| TAC | GGC | GGT | ATC | TCC | TCC | CGA | AGC | GAA | TGT | GAT | AGC | TAC | CCC | GAG | CTT | 642 |
| Tyr | Gly | Gly | Ile 170 | Ser | Ser | Arg | Ser | Glu 175 | Cys | Asp | Ser | Tyr | Pro 180 | Glu | Leu | |
| CTC | AAG | GAC | GGT | TGC | CAC | TGG | CGA | TTC | GAC | TGG | TTC | GAG | AAC | GCC | GAC | 690 |
| Leu | Lys | Asp 185 | Gly | Cys | His | Trp | Arg 190 | Phe | Asp | Trp | Phe | Glu 195 | Asn | Ala | Asp | |
| AAC | CCT | GAC | TTC | ACC | TTT | GAG | CAG | GTT | CAG | TGC | CCC | AAG | GCT | CTC | CTC | 738 |
| Asn | Pro 200 | Asp | Phe | Thr | Phe | Glu 205 | Gln | Val | Gln | Cys | Pro 210 | Lys | Ala | Leu | Leu | |
| GAC | ATC | AGT | GGA | TGC | AAG | CGT | GAT | GAC | GAC | TCC | AGC | TTC | CCT | GCC | TTC | 786 |
| Asp | Ile 215 | Ser | Gly | Cys | Lys 220 | Arg | Asp | Asp | Asp | Ser 225 | Ser | Phe | Pro | Ala | Phe 230 | |
| AAG | GTT | GAT | ACC | TCG | GCC | AGC | AAG | CCC | CAG | CCC | TCC | AGC | TCC | GCT | AAG | 834 |
| Lys | Val | Asp | Thr | Ser 235 | Ala | Ser | Lys | Pro | Gln 240 | Pro | Ser | Ser | Ser | Ala 245 | Lys | |
| AAG | ACC | ACC | TCC | GCT | GCT | GCT | GCC | GCT | CAG | CCC | CAG | AAG | ACC | AAG | GAT | 882 |
| Lys | Thr | Thr | Ser 250 | Ala | Ala | Ala | Ala | Ala 255 | Gln | Pro | Gln | Lys | Thr 260 | Lys | Asp | |
| TCC | GCT | CCT | GTT | GTC | CAG | AAG | TCC | TCC | ACC | AAG | CCT | GCC | GCT | CAG | CCC | 930 |
| Ser | Ala | Pro 265 | Val | Val | Gln | Lys | Ser 270 | Ser | Thr | Lys | Pro | Ala 275 | Ala | Gln | Pro | |
| GAG | CCT | ACT | AAG | CCC | GCC | GAC | AAG | CCC | CAG | ACC | GAC | AAG | CCT | GTC | GCC | 978 |
| Glu | Pro 280 | Thr | Lys | Pro | Ala | Asp 285 | Lys | Pro | Gln | Thr | Asp 290 | Lys | Pro | Val | Ala | |
| ACC | AAG | CCT | GCT | GCT | ACC | AAG | CCC | GTC | CAA | CCT | GTC | AAC | AAG | CCC | AAG | 1026 |
| Thr 295 | Lys | Pro | Ala | Ala | Thr 300 | Lys | Pro | Val | Gln | Pro 305 | Val | Asn | Lys | Pro | Lys 310 | |
| ACA | ACC | CAG | AAG | GTC | CGT | GGA | ACC | AAA | ACC | CGA | GGA | AGC | TGC | CCG | GCC | 1074 |
| Thr | Thr | Gln | Lys | Val 315 | Arg | Gly | Thr | Lys | Thr 320 | Arg | Gly | Ser | Cys | Pro 325 | Ala | |
| AAG | ACT | GAC | GCT | ACC | GCC | AAG | GCC | TCC | GTT | GTC | CCT | GCT | TAT | TAC | CAG | 1122 |
| Lys | Thr | Asp | Ala 330 | Thr | Ala | Lys | Ala | Ser 335 | Val | Val | Pro | Ala | Tyr 340 | Tyr | Gln | |
| TGT | GGT | GGT | TCC | AAG | TCC | GCT | TAT | CCC | AAC | GGC | AAC | CTC | GCT | TGC | GCT | 1170 |
| Cys | Gly | Gly 345 | Ser | Lys | Ser | Ala | Tyr 350 | Pro | Asn | Gly | Asn | Leu 355 | Ala | Cys | Ala | |
| ACT | GGA | AGC | AAG | TGT | GTC | AAG | CAG | AAC | GAG | TAC | TAC | TCC | CAG | TGT | GTC | 1218 |
| Thr | Gly | Ser 360 | Lys | Cys | Val | Lys 365 | Gln | Asn | Glu | Tyr | Tyr 370 | Ser | Gln | Cys | Val | |
| CCC | AAC | TAAATGGTAG | ATCCATCGGT | TGTGGAAGAG | ACTATGCGTC | TCAGAAGGGA | | | | | | | | | | 1274 |
| Pro 375 | Asn | | | | | | | | | | | | | | | |

TCCTCTCATG AGCAGGCTTG TCATTGTATA GCATGGCATC CTGGACCAAG TGTTCGACCC 1334

TTGTTGTACA TAGTATATCT TCATTGTATA TATTTAGACA CATAGATAGC CTCTTGTCAG 1394

SEQUENCE DESCRIPTION:
CGACAACTGG CTACAAAAGA CTTGGCAGGC TTGTTCAATA TTGACACAGT TTCCTCCATA 1454

AAAAAAAAAA AAAAAAAA 1473

| Met 1 | Arg | Ser | Tyr | Thr 5 | Leu | Leu | Ala | Leu | Ala 10 | Gly | Pro | Leu | Ala | Val 15 | Ser |
|---|---|---|---|---|---|---|---|---|---|---|---|---|---|---|---|
| Ala | Ala | Ser | Gly 20 | Ser | Gly | His | Ser | Thr 25 | Arg | Tyr | Trp | Asp | Cys 30 | Cys | Lys |
| Pro | Ser | Cys 35 | Ser | Trp | Ser | Gly | Lys 40 | Ala | Ala | Val | Asn | Ala 45 | Pro | Ala | Leu |
| Thr | Cys 50 | Asp | Lys | Asn | Asp | Asn 55 | Pro | Ile | Ser | Asn | Thr 60 | Asn | Ala | Val | Asn |
| Gly 65 | Cys | Glu | Gly | Gly | Gly 70 | Ser | Ala | Tyr | Ala | Cys 75 | Thr | Asn | Tyr | Ser | Pro 80 |
| Trp | Ala | Val | Asn | Asp 85 | Glu | Leu | Ala | Tyr | Gly 90 | Phe | Ala | Ala | Thr | Lys 95 | Ile |
| Ser | Gly | Gly | Ser 100 | Glu | Ala | Ser | Trp | Cys 105 | Cys | Ala | Cys | Tyr | Ala 110 | Leu | Thr |
| Phe | Thr | Thr 115 | Gly | Pro | Val | Lys | Gly 120 | Lys | Lys | Met | Ile | Val 125 | Gln | Ser | Thr |
| Asn | Thr 130 | Gly | Gly | Asp | Leu | Gly 135 | Asp | Asn | His | Phe | Asp 140 | Leu | Met | Met | Pro |
| Gly 145 | Gly | Gly | Val | Gly | Ile 150 | Phe | Asp | Gly | Cys | Thr 155 | Ser | Glu | Phe | Gly | Lys 160 |
| Ala | Leu | Gly | Gly | Ala 165 | Gln | Tyr | Gly | Gly | Ile 170 | Ser | Ser | Arg | Ser | Glu 175 | Cys |
| Asp | Ser | Tyr | Pro 180 | Glu | Leu | Leu | Lys | Asp 185 | Gly | Cys | His | Trp | Arg 190 | Phe | Asp |
| Trp | Phe | Glu 195 | Asn | Ala | Asp | Asn | Pro 200 | Asp | Phe | Thr | Phe | Glu 205 | Gln | Val | Gln |
| Cys | Pro 210 | Lys | Ala | Leu | Leu | Asp 215 | Ile | Ser | Gly | Cys | Lys 220 | Arg | Asp | Asp | Asp |
| Ser 225 | Ser | Phe | Pro | Ala | Phe 230 | Lys | Val | Asp | Thr | Ser 235 | Ala | Ser | Lys | Pro | Gln 240 |
| Pro | Ser | Ser | Ser | Ala 245 | Lys | Lys | Thr | Thr | Ser 250 | Ala | Ala | Ala | Ala | Ala 255 | Gln |
| Pro | Gln | Lys | Thr 260 | Lys | Asp | Ser | Ala | Pro 265 | Val | Val | Gln | Lys | Ser 270 | Ser | Thr |
| Lys | Pro | Ala 275 | Ala | Gln | Pro | Glu | Pro 280 | Thr | Lys | Pro | Ala | Asp 285 | Lys | Pro | Gln |
| Thr | Asp 290 | Lys | Pro | Val | Ala | Thr 295 | Lys | Pro | Ala | Ala | Thr 300 | Lys | Pro | Val | Gln |
| Pro 305 | Val | Asn | Lys | Pro | Lys 310 | Thr | Thr | Gln | Lys | Val 315 | Arg | Gly | Thr | Lys | Thr 320 |
| Arg | Gly | Ser | Cys | Pro 325 | Ala | Lys | Thr | Asp | Ala 330 | Thr | Ala | Lys | Ala | Ser 335 | Val |
| Val | Pro | Ala | Tyr 340 | Tyr | Gln | Cys | Gly | Gly 345 | Ser | Lys | Ser | Ala | Tyr 350 | Pro | Asn |
| Gly | Asn | Leu 355 | Ala | Cys | Ala | Thr | Gly 360 | Ser | Lys | Cys | Val | Lys 365 | Gln | Asn | Glu |
| Tyr | Tyr 370 | Ser | Gln | Cys | Val | Pro 375 | Asn | | | | | | | | |

We claim:

1. A detergent composition comprising:

(a) a quaternary ammonium compound of the formula $$R_1R_2R_3R_4N^+X^-$$

wherein $R_1$ is $C_8$–$C_{16}$ alkyl, each of $R_2$, $R_3$ and $R_4$ is independently $C_1$–$C_4$ alkyl or hydroxyl alkyl, benzyl, or —$(C_2H_4O)_xH$ where x has a value from 2 to 5, not more than one of $R_2$, $R_3$ or $R_4$ being benzyl and $X^-$ is an anion, and (b) a cellulase wherein said cellulase consists essentially of a homogeneous endoglucanase component which is immunoreactive with an antibody raised against a highly purified about 43 kD cellulase derived from *Humicola insolens*, DSM 1800.

2. A detergent composition according to claim 1, wherein the endoglucanase component of said cellulase has an isoelectric point of about 5.1.

3. A detergent composition according to claim 2 wherein said endoglucanase component is producible by a method comprising cultivating a host cell transformed with a recombinant DNA vector carrying a DNA sequence encoding said endoglucanase component or a precursor of said endoglucanase component, as well as DNA sequences encoding functions permitting the expression of the DNA sequence encoding the endoglucanase component, or a precursor thereof, in a culture medium under conditions permitting the expression of the endoglucanase component or precursor thereof and recovering the endoglucanase component form the culture.

4. A detergent composition according to claim 1 wherein the cellulase has the amino acid sequence shown in the appended sequence listing ID #2, or is a homologue thereof exhibiting endoglucanase activity.

5. A detergent composition according to claim 2 wherein said cellulase is producible by a species of Humicola.

6. A detergent composition according to claim 1 characterized in that the cellulase compound is and endoglucanase enzyme having the amino acid sequence shown in the appended sequence lising ID #4, or is a homologue thereof exhibiting endoglucanase activity.

7. A detergent composition according to claim wherein said endoglucanase enzyme is producible by a species of Fusarium.

8. A detergent composition according to claim 5, 6, or 7 wherein said enzyme is produced by a DNA construct comprising a DNA sequence encoding the enzyme.

9. A detergent composition according to claim 8 wherein the DNA sequence is as shown in the appended sequence listings ID #1 or ID #3.

10. A detergent composition according to claim 4, 5, 6 or 7 wherein said host cell is a strain of fungus selected from the group consisting of Tricloderuca or Aspergillus, or a yeast cell selected from the group consisting of Hansenula or Saccharomyces.

11. A detergent composition according to claim 4, 5, 6 or 7 wherein said host cell is a strain of a bacterium selected from the group consisting of Bacillus, Streptomyces or *E. coli*.

12. A detergent composition according to claim 1, 2, 3, 4, 5, 6 or 7 wherein the water soluble cationic compound is selected from quaternary ammonium salts in which $R_1$ is $C_{12}$–$C_{14}$ alkyl and $R_2$, $R_3$ and $R_4$ are selected from methyl and hydroxyethyl groups.

13. A detergent composition according to claim 1, 2, 3, 4, 5, 6 or 7 wherein the level of said watersoluble cationic compound is from 0.2 to 10%.

14. A detergent composition according to claim 1, 2, 3, 4, 5, 6, or 7 further comprising anionic surfactants, wherein the molar ratio of the anionic surfactant to the water soluble quaternary ammonium compound is greater than 1:1.

15. A detergent composition according to claim 1, 2, 3, 4, 5, 6, or 7 which is a detergent additive, in the form of a non-dusting granulate or liquid.

16. A detergent composition which comprises a detergent additive according to claim 1, 2, 3, 4, 5, 6 or 7.

17. A detergent composition according to claim 16 which is in granular form, compact granular form or liquid form.

18. A laundry process comprising contacting fabrics with a detergent composition according to claim 1, 2, 3, 4, 5, 6 or 7, wherein the cellulase being added at levels of from 0.005 to 40 mg enzyme protein/liter of wash solution.

* * * * *